(12) United States Patent
Bilstad et al.

(10) Patent No.: US 7,264,771 B2
(45) Date of Patent: Sep. 4, 2007

(54) METHOD AND APPARATUS FOR MANIPULATING PRE-STERILIZED COMPONENTS IN AN ACTIVE STERILE FIELD

(75) Inventors: Arnold C. Bilstad, Deerfield, IL (US); Bradley H. Buchanan, Ross, CA (US); Alan W. Martilla, Waukegan, IL (US); Archie Woodworth, Barrington, IL (US)

(73) Assignee: Baxter International Inc., Deerfield, IL (US)

( * ) Notice: Subject to any disclaimer, the term of this patent is extended or adjusted under 35 U.S.C. 154(b) by 1826 days.

(21) Appl. No.: 09/294,964

(22) Filed: Apr. 20, 1999

(65) Prior Publication Data

US 2002/0006353 A1 Jan. 17, 2002

(51) Int. Cl.
*A61L 2/00* (2006.01)
(52) U.S. Cl. ............. 422/22; 250/435.11; 250/455.11; 250/492.3; 422/24
(58) Field of Classification Search ............. 422/22, 422/24, 37; 250/492.3, 492.1, 398, 435, 250/453.11, 455.11
See application file for complete search history.

(56) References Cited

U.S. PATENT DOCUMENTS

| | | | | |
|---|---|---|---|---|
| 3,780,308 A | 12/1973 | Nablo | | 250/492 |
| 3,809,768 A | 5/1974 | Berry | | 426/309 |
| 3,968,195 A | 7/1976 | Bishop | | 264/154 |
| 4,157,723 A * | 6/1979 | Granzow et al. | | 141/1 |
| 4,209,013 A | 6/1980 | Alexander et al. | | 128/213 |
| 4,242,310 A | 12/1980 | Greff et al. | | 422/300 |
| 4,265,279 A | 5/1981 | Weikert | | 141/10 |
| 4,507,119 A | 3/1985 | Spencer | | 604/280 |
| 4,521,263 A | 6/1985 | Benin et al. | | 156/159 |
| RE32,056 E | 12/1985 | Granzow et al. | | 141/1 |
| 4,588,402 A | 5/1986 | Igari et al. | | 604/408 |

(Continued)

FOREIGN PATENT DOCUMENTS

EP 87 30 1791 3/1987

(Continued)

OTHER PUBLICATIONS

"More Efficient, Less Expensive Electron Beam Processing," *Science & Technology Review*, Nov./Dec. 1995, pp. 32-33. A.I.T., Inc. Brochure on Model CBT-101 LAB Table-Top Electron Beam Processor (1995).

*Primary Examiner*—Krisanne Jastrzab
(74) *Attorney, Agent, or Firm*—Austin J. Foley; Bell, Boyd & Lloyd LLP

(57) ABSTRACT

The connection, assembly, or fill of two or more pre-sterilized components having at least one terminal end each for attachment to another component, and an apparatus for performing such a connection, while maintaining the sterility of the components is disclosed. The resulting connection is made permanent by bonding the contacting components together using either a solvent bonding technique, a radio frequency sealer, a heat sealer, or any other suitable process. The connection is preferably made within an active sterile field. Using a low-voltage electron beam instrument, such as the MIN-EB™, a suitable sterile field sphere can be created. The terminal ends of the multiple components remain within the sterile field sphere until the possibility of contamination within the sealed components is significantly reduced to industry acceptable standards.

40 Claims, 7 Drawing Sheets

U.S. PATENT DOCUMENTS

| | | | |
|---|---|---|---|
| 4,910,435 A | 3/1990 | Wakalopulos | 315/111.31 |
| 5,009,654 A | 4/1991 | Minshall et al. | 604/410 |
| 5,215,636 A | 6/1993 | Danilychev et al. | 422/186.05 |
| 5,352,210 A | 10/1994 | Marrucchi | 604/180 |
| 5,414,267 A * | 5/1995 | Wakalopulos | 250/492.3 |
| 5,496,302 A | 3/1996 | Minshall et al. | 604/410 |
| 5,557,163 A | 9/1996 | Wakalopulos | 313/420 |
| 5,612,588 A | 3/1997 | Wakalopulos | 313/420 |
| 5,637,953 A | 6/1997 | Wakalopulos | 313/420 |
| 5,645,796 A * | 7/1997 | Caputo et al. | 422/22 |
| 5,802,689 A | 9/1998 | Sano | 29/33 |
| 6,022,339 A | 2/2000 | Fowles et al. | 604/411 |
| 6,140,657 A | 10/2000 | Wakalopulos et al. | 250/492.3 |
| 6,191,424 B1 | 2/2001 | Stirling et al. | 250/455.11 |

FOREIGN PATENT DOCUMENTS

| | | |
|---|---|---|
| EP | 0 236 107 A1 | 9/1987 |
| EP | 89 30 9806 | 9/1989 |
| FR | 2509689 | 7/1981 |
| FR | 2 567 406 A1 | 1/1986 |
| JP | 60-99254 | 6/1985 |
| WO | WO 85/00979 | 3/1985 |

* cited by examiner

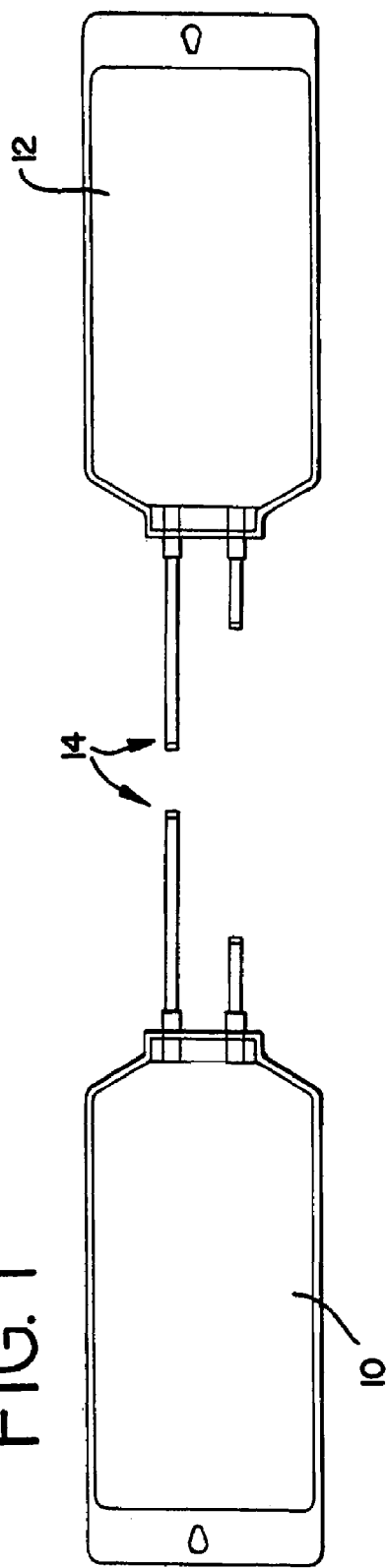
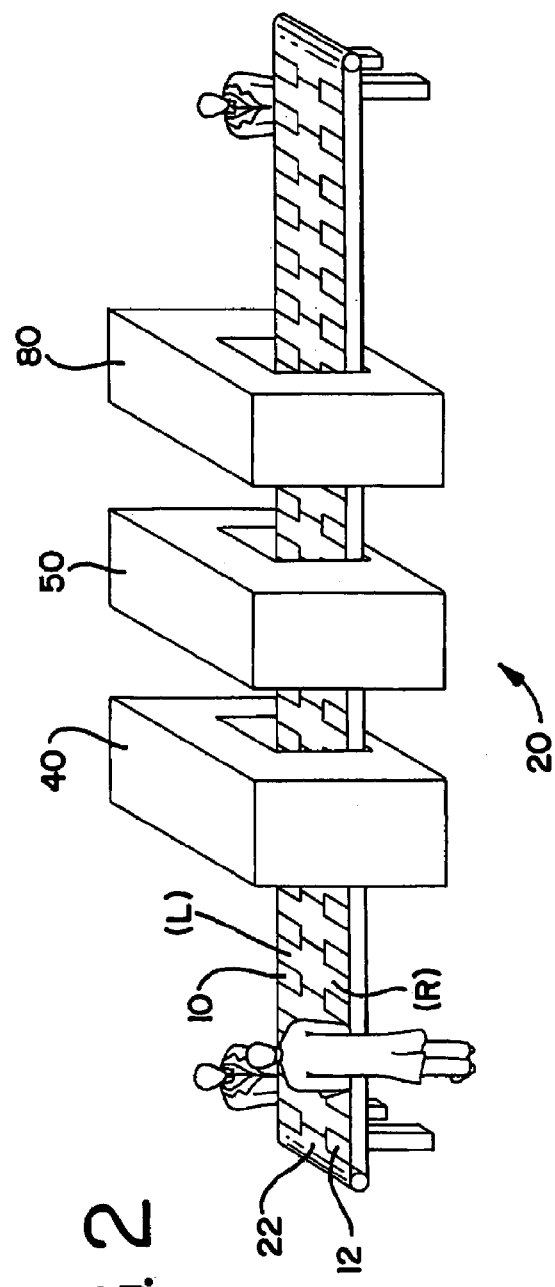

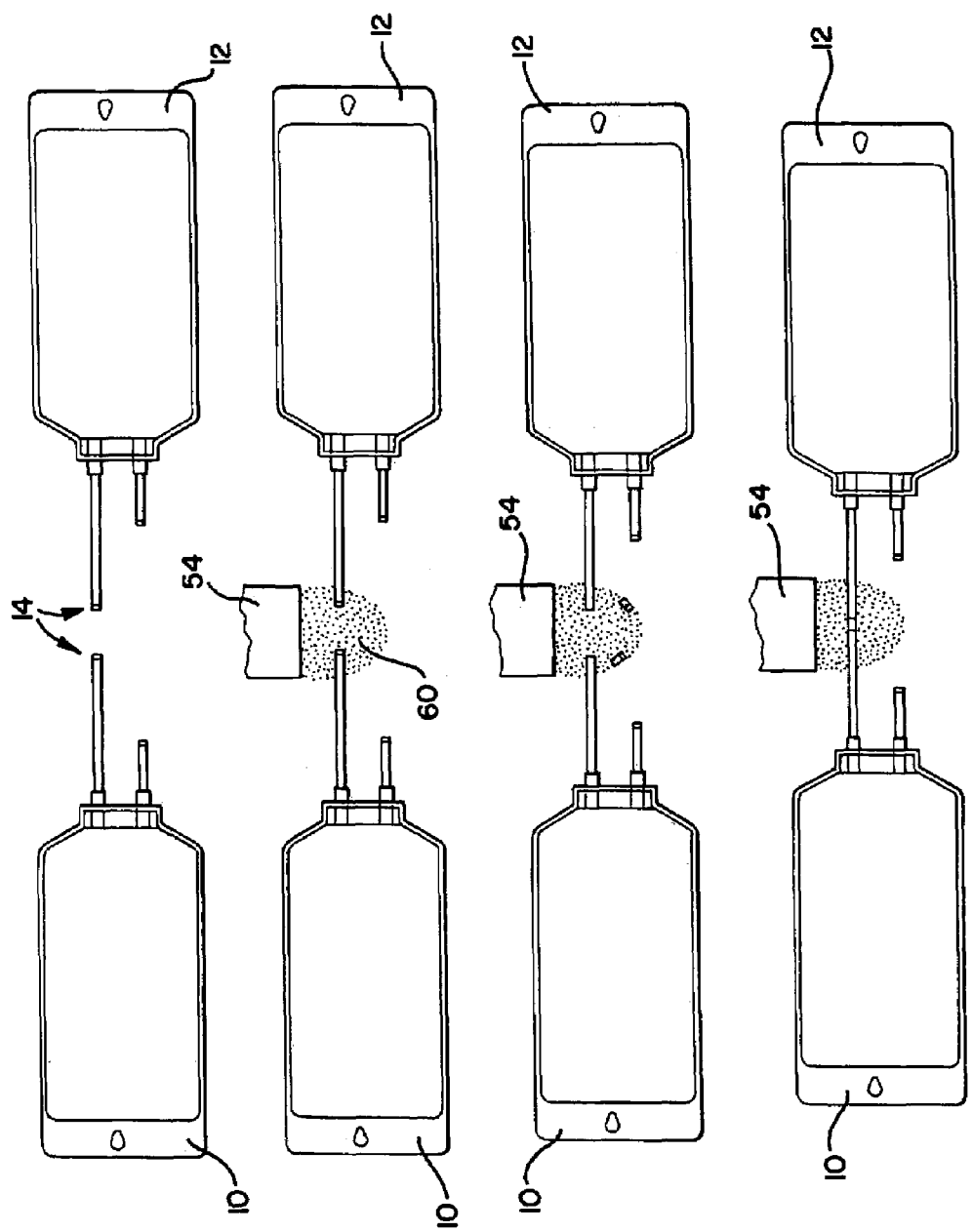

METHOD AND APPARATUS FOR MANIPULATING PRE-STERILIZED COMPONENTS IN AN ACTIVE STERILE FIELD

TECHNICAL FIELD

This invention relates generally to the methods and apparatus for connecting, assembling, and filling pre-sterilized medical components in a sterile field. More particularly, the present invention relates to the use of a low voltage electron beam field to create a sterile atmosphere in which connecting, assembling, or filling of pre-sterilized medical components, such as solution delivery sets, medical tubing, drug vials, medical containers, and the like, may occur such that the sterility of the product is continuously maintained.

BACKGROUND ART

Pre-sterilized, disposable medical products are commonplace in the United States, and other countries throughout the world. One significant restraint on the design, development, and manufacture of such products has been the fact that certain desirable products would include portions or components which are mutually incompatible from a sterilization standpoint. For example, it may be desirable to provide a unitary, pre-sterilized product which has a sealed liquid or powder drug component and a plastic apparatus component, such as a tubing or flow control set.

The integral product, however, cannot be sterilized after assembly because not all of the components may be subjected to the same form of sterilization. That is, the plastic apparatus component (e.g., the tubing or flow control device) may only be capable of sterilization with radiation or gas. The drug component, on the other hand, may not be sterilized with either gas or radiation—gas sterilization would be ineffective to sterilize a sealed drug, while exposing the drug to radiation may lead to product degradation or otherwise have a deleterious effect on the drug.

Accordingly, efforts have been made to devise a method or means for joining, in a sterile manner, components which are individually pre-sterilized. Such efforts have included the use of electron beam accelerators to sterilize the compromised portion of the assembled components. Electron beam sterilization is a well-known and accepted technique for terminally sterilizing disposable medical devices. Existing electron beam systems are high voltage devices whose electrons completely penetrate the materials being sterilized. Such a device and method is disclosed in U.S. Pat. Nos. 5,009,654 and 5,496,302, both to Minshall et al., and both assigned to Baxter International Inc.

The electron beam used in Minshall et al. is derived from a high energy (>0.3 MeV or 300 KeV) instrument to "achieve sterilization at the tubing center." Energy levels of 1.1 MeV, 0.9 MeV, 0.75 MeV, and 0.6 MeV are disclosed for sterilization. The high energy process involves clamping the tubing to be connected together close to their terminal ends. Then the terminal ends are cutoff and the open ended tubings are bonded or welded together. Before the new fluid pathway is opened, the high energy electron beam is applied between the two clamps to effect sterilization. While these type of high energy systems function well, when compared to the present invention they can be considered very large (sometimes requiring a separate room with thick walls of lead shielding), more expensive, and somewhat product-specific.

Another example of creating a sterile connection is disclosed in U.S. Pat. No. 4,157,723 and Reissue No. 32,056 to Granzow et al., each assigned to assignee of the present invention. The Granzow et al. invention is based upon a clear TPX unisex connector housing containing an integral black TPX (carbon doped) disk. The connectors are attached to tubing from, for example, a solution container that has been steam sterilized, which is connected to similar tubing from a solution delivery set which has been ethylene oxide (EtO) or Gamma sterilized. Snapping two connectors together and applying an intense focused light beam on the black disks quickly melts them together to form an annular ring that completes the sterile fluid path and effects a sterile connection. Subsequent to connection, the solutions would be transferred to empty solution containers, while the sterile connectors, including the original solution containers, were removed and discarded. Although functional, the present invention provides a method which improves the rate and cost of this process.

E.I. Du Pont developed and patented a "Hot Knife" tubing to tubing connection system, as shown in U.S. Pat. No. 4,521,263 to Benin et al. In this system, two thermoplastic tubes with sealed ends facing each other are placed side by side in a fixture incorporating a special heated knife blade. A connection is made by (1) cutting through both tubes with the heated knife blade, (2) shuttling the tubes to be connected into alignment on each side of the heated knife blade, and (3) removing the heated knife blade while pushing the tubes together. This system can be more expensive to use than the present invention because it requires the use of a new disposable knife blade for each connection made.

The apparatus and methods of the present invention overcome the disadvantages of other prior art techniques. The present invention is focused on maintaining the sterility of the pre-sterilized components during assembly, connection, and fill, rather than attempting to effect sterilization after such manipulations, like the processes used extensively by those skilled in the art. Additionally, the present invention is focused on processes which are far less expensive than techniques utilizing disposable parts.

SUMMARY OF THE INVENTION

In accordance with this invention, a new apparatus and method for forming a connection, and particularly a sterile connection, between two or more pre-sterilized components is disclosed. Preferably, each of the components has at least one closed end suitable for connecting to another component. An embodiment of the present method and apparatus requires sterilizing an end of each component to be connected with an active sterile field, then opening the closed ends of the components within the active sterile field. The sterile connection is completed by connecting the opened ends together while in the active sterile field.

It is further an aspect of the present invention to provide an apparatus and method for forming a sterile assembly between two or more pre-sterilized components. Preferably, each of the components has at least one closed end suitable for connecting to another component. An embodiment of the present method and apparatus requires sterilizing an end of each component to be assembled together with an active sterile field, then assembling the ends together while in the active sterile field.

It is still a further aspect of the present invention to provide an apparatus and method for performing a sterile fill of a pre-sterilized container with a pre-sterilized liquid component from a bulk container. Preferably, the empty container has at least one end suitable for accepting the liquid component, and the bulk container has at least one end suitable for delivery of the liquid. An embodiment of the present method and apparatus requires sterilizing a suitable end of each component with an active sterile field, then filling the empty container with an aliquot of liquid from the bulk container while the ends are in the active sterile field.

Specifically, in one embodiment of the present methods, sterilization of the ends of each component is achieved by creating an electron beam field to produce an active sterile field, and then positioning the ends within the electron beam field. The present method preferably uses an electron beam field established at a voltage of less than 300 Kev. More specifically, the electron beam field is established at a voltage within a range of about 30 to about 300 Kev.

In another embodiment of the present invention, sterilization of the ends of each component is achieved by creating a chemical vapor atmosphere to produce an active sterile field, and then positioning the ends within the sterile chemical vapor atmosphere. The chemical vapor atmosphere may be comprised of hydrogen peroxide, peracetic acid, chlorine dioxide, or any other suitable chemical vapor.

In still another embodiment of the present invention, sterilization of the ends of each component is achieved by using a high energy pulsed light with a large ultraviolet component to produce an active sterile field, and then positioning the ends within the pulsed light.

Still one more embodiment for sterilizing the ends of each component is achieved by creating a plasma atmosphere to produce an active sterile field, and then positioning the ends within the plasma atmosphere.

With respect to the apparatus of the present invention, a device is disclosed for effecting the sterile connection, sterile assembly, or sterile filling using at least two pre-sterilized components, each component preferably having at least one end for connecting to at least another component. One embodiment of the invention comprises an active sterile field for encompassing the ends of the components to be connected, assembled, or filled while a surface supports the ends of the pre-sterilized components within the active sterile field.

One embodiment may have a mechanism which severs the ends of the pre-sterilized components while supported by the surface in the active sterile field to create open ends, as well as a mechanism which brings the opened ends into aligned contact with each other while supported by the surface in the active sterile field. The apparatus is completed by a sealing device which joins the opened ends together.

Other advantages and aspects of the present invention will become apparent upon reading the following detailed description of the invention.

DESCRIPTION OF THE DRAWINGS

FIG. 1 illustrates the positioning of two components, a filled wet container and an empty dry container, before undergoing sterile field connection;

FIG. 2 illustrates the assembly line configuration of one embodiment of the present invention;

FIGS. 3A through 3D illustrate an embodiment of present method for effecting a sterile connection of two components within an active sterile field;

DETAILED DISCLOSURE OF PREFERRED EMBODIMENT

Figure 4:
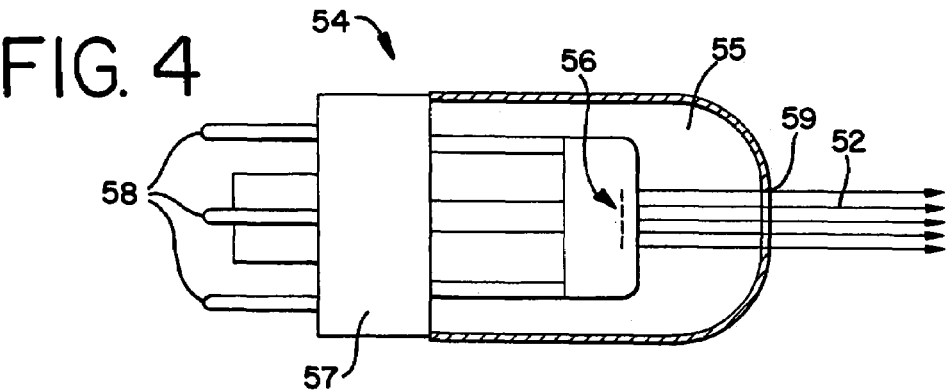
FIG. 4 is an illustration of an electron beam tube used in an embodiment of the present invention.

While the invention is susceptible of embodiment in many different forms, this disclosure will describe in detail preferred embodiments of the invention with the understanding that the present disclosure is to be considered as an exemplification of the principles of the invention and is not intended to limit the broad aspect of the invention to the embodiments illustrated.

The present invention involves methods and apparatus for joining plastic components in a sterile manner. The term "joining" in this application includes the processes of: 1) connecting components, where a fluid pathway is created at the time of joining; 2) assembling components, where a fluid pathway is not complete at joining, but may be completed at a later time; and, 3) filling at least one component from a bulk container. Particularly, the invention permits the joining together of tubing to container, tubing to tubing, tubing to connector, vial to connector, container to connector, and even sheet/film stock to itself, in a sterile field.

The drawings and following discussion reference components 10, 12, as an empty dry container and a filled wet container, respectively. These components are typically pre-sterilized by different methods, such as gamma radiation, steam sterilization, chemical vapor, high-voltage electron beam radiation, or the like.

The low-voltage electron beam instrument is the preferred source for the active sterile field. Suitable examples of such a device are fully discussed in U.S. Pat. Nos. 4,910,435 and 5,612,588, both to Wakalopulos and assigned to American International Technologies, Inc. of Torrance, Calif. The disclosure of each of these Wakalopulos patents is hereby incorporated by reference. Particularly, a suitable low-voltage electron beam source is manufactured by American International Technologies, Inc. under the trade name MIN-EB™. The MIN-EB™ is capable of operating at a relatively low voltage, within the range of about 30 KeV to about 100 KeV. This is the preferred operation range of the present invention, including all combination and sub-combination of ranges within this range.

Referring to the drawings, components 10, 12, are more readily understood in FIG. 1. Each component preferably has a terminal sealed end 14 attached thereto. The sealed ends 14 of components 10, 12 may be identical, or as shown in FIGS. 7A through 7E, several alternative configurations may be provided. Other variations (not shown) of the sealed ends 14 are also possible. Connecting the end types together may be handled differently for each type, but those skilled in the relevant art would understand the necessary modifications to accommodate such design variations.

FIG. 2 illustrates a general assembly line production concept for a sterile joining system 20. Such a mass production system, it is anticipated, would provide many benefits throughout the industry. Components 10, 12 are shown spaced along the sterile joining system 20 at various stages of the process. FIG. 2 shows the sterile joining system 20 comprised of a support surface 22 extending the length of the system. This surface, when divided lengthwise, has a left half (L) and a right half (R). Components 10, 12 are shown arranged in pairs on support surface 22, with component 10 along the left side (L) of surface 22 and component 12 along the right side (R). The support surface 22 may be a conveyor belt, or similar moving surface, to automatically transport components 10, 12 through the system 20. Sterile filling using a bulk container may use only a single line of empty components, as will be more fully understood later in this disclosure.

The arranged components 10, 12 are first optionally conveyed to a labeling station 40 where important batch, lot, and date codes may be applied. Components 10, 12 are then conveyed to the active sterile field station 50 where a sterile connection between the pre-sterilized components may be effected. This process is better illustrated in FIGS. 3A through 3D.

FIGS. 3A-3D show an electron beam (e-beam) field 60 created within station 50. Electron beam 60 is created by the tube 54 as illustrated in FIG. 4. Tube 54 comprises a vacuum tube 55 shrouding filament 56 on all sides, except at base 57. Base 57 has various electrical connectors 58 for plugging into a low voltage source. Opposite base 57 is a thin film window 59 which discharges the electron beam toward the desired location. Window 59 is approximately 3 microns thick, and through it a beam of approximately 2 mm×25 mm (0.08"×1") area is discharged. Arrays of tubes 54 could be set up to increase the collective area of the e-beam discharge. An example of this arrangement is illustrated in U.S. Pat. No. 5,414,267 (or Re. 35,203) to Wakalopulos, the disclosure of which is hereby incorporated by reference.

Tube 54 is preferably about 5 cm (2") from the area in which an active sterile field is desired and operates at about 60 KeV. Higher voltages may allow a greater gap, and a lower voltage might require a lesser gap. FIG. 3A shows the pre-sterilized components 10, 12 arranged prior to connection. Tube 54 creates the spherical-shaped e-beam field 60 having approximately a two-inch diameter. Other diameters of the sterile field are certainly possible, however manipulation of the joining of components requires very little space. Where a greater space is required, field 60 could be made larger by conventional methods.

Referring to FIG. 3B, the ends 14 of components 10, 12 are conveyed into the sterile e-beam field 60. While maintained within sphere 60, ends 14 of each component 10, 12 may be cut-off, as shown in FIG. 3C, to create opened ends. The mechanism for opening these ends may be a mechanical blade, which may be held permanently within the e-beam field 60 to maintain its sterility, or any other suitable cutting or opening mechanism. FIG. 3D shows that once the ends 14 are cut-off, the resulting open ends are connected together while still within the field 60.

While the use of an electron beam field is a preferred source for creating the active sterile field, applicants of the present invention have anticipated the use of alternative sources, such as a chemical vapor atmosphere. A chemical vapor atmosphere can be created through known methods, and the chemical may be selected from the group comprising hydrogen peroxide, peracetic acid, chlorine dioxide, or any other suitable chemical compound. Similarly, a plasma atmosphere, such as ozone (not shown), may be created, using any of the commonly known methods, to achieve a sterile field. A pulsed high-energy light may also be suitable for creating the desired active sterile field. These alternate sources, however, may not provide the same size and cost advantages of the preferred electron beam source.

Figure 5A:
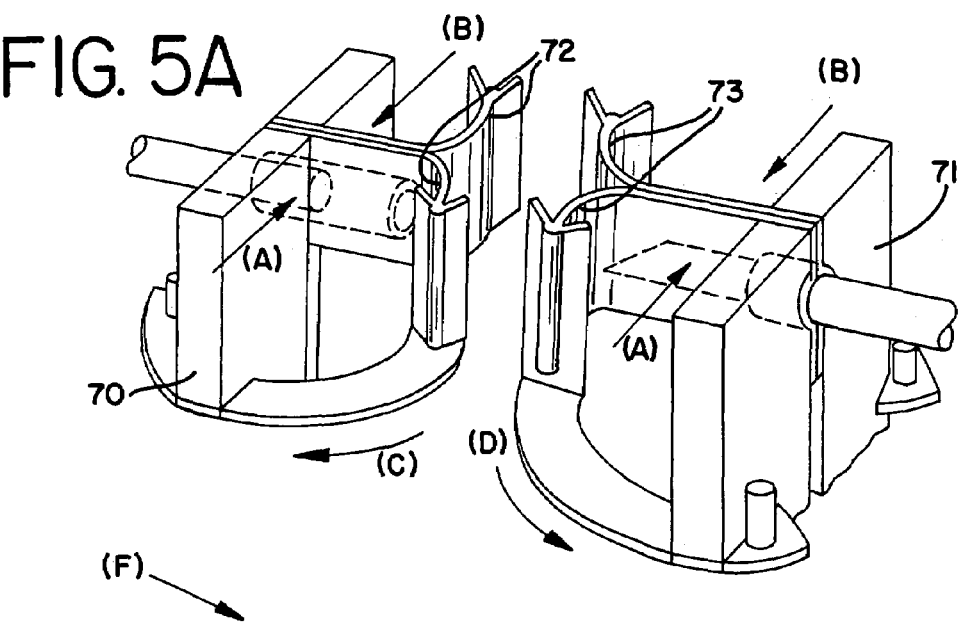
FIG. 5A is one embodiment of a mechanism for supporting the ends of multiple components within an active sterile field.
Figure 5B:
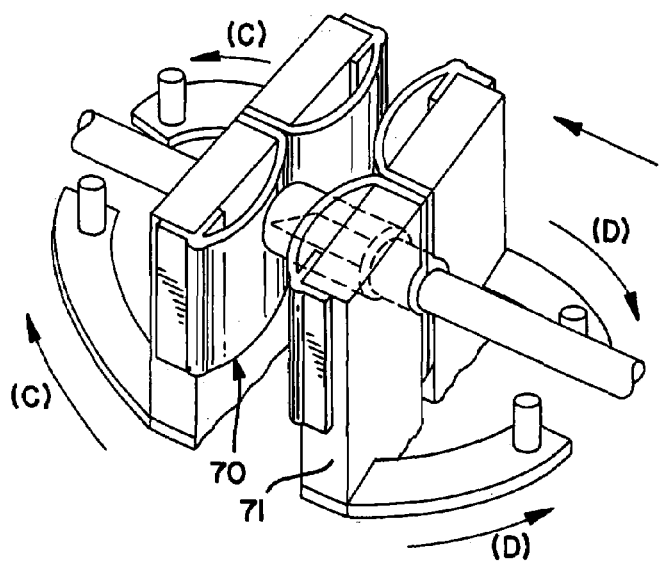
FIG. 5B shows the mechanism of FIG. 5A as the ends of multiple components are brought into contact with each other within an active sterile field.
Figure 6A:
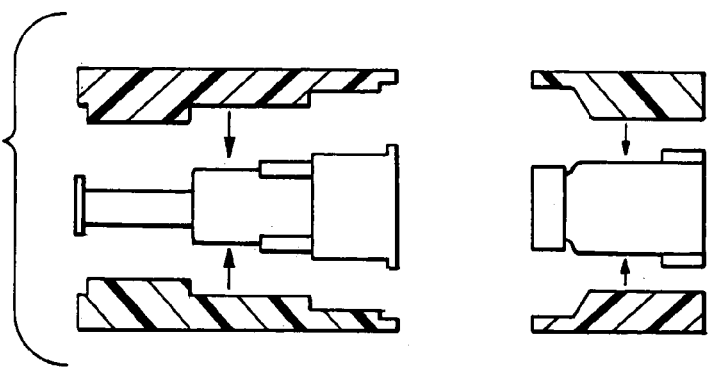
FIGS. 6A through 6D illustrate an alternative use of the present invention for the sterile assembly of a pre-sterilized vial to a pre-sterilized device.
Figure 6B:
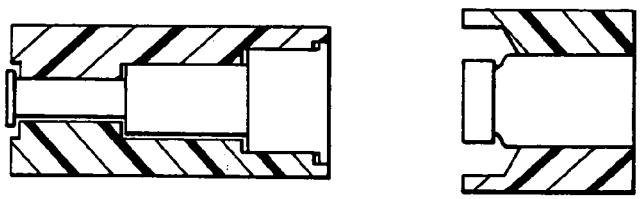
Figure 6C:
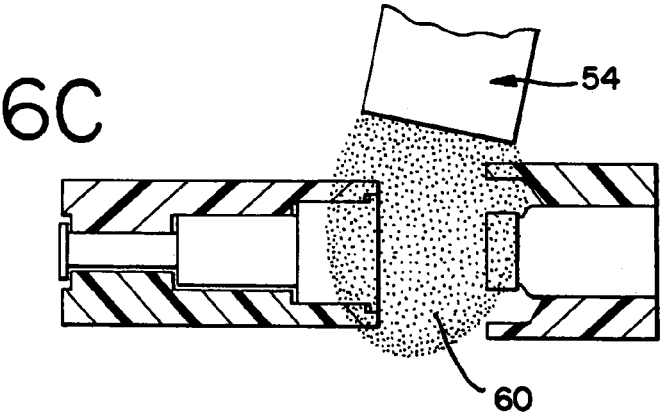
Figure 6D:
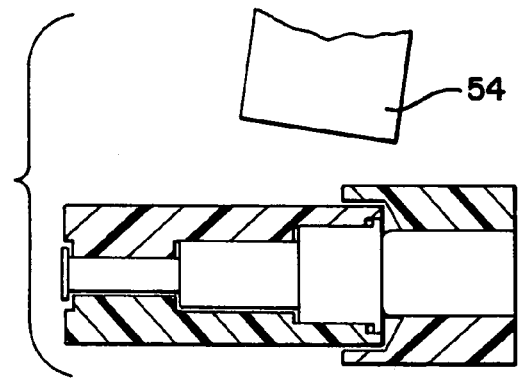

Connection of the opened ends together while still within the e-beam field 60 may be achieved in a variety of ways. FIGS. 5A and 5B illustrate one possible mechanism for bringing the opened ends into aligned contact with each other. The mechanism uses a pair of automated clamps 70, 71 which engage a portion of components 10, 12, respectively, just behind ends 14, as shown in FIG. 5A. Clamps 70, 71 close about components 10, 12 by actuation in the direction of arrows (A,B). Clamps 70, 71 have a pair of rotating tabs 72, 73 which help to maintain the alignment of ends 14 of components 10, 12. Upon rotation of tabs 72, 73 in the direction of arrows (C,D), ends 14 of components 10, 12 are exposed within the e-beam field (See FIG. 3B) from tube 54. A short delay of approximately 2-3 seconds allows the e-beam to sterilize the surface of the ends 14 before they are opened.

The type of connection to be made will determine how the opened ends of components 10, 12 are brought into contact with one another. FIGS. 5A and 5B illustrate the use of a spike tube and a membrane tube. With the spike and membrane configuration, cut-off of the ends 14 is not necessary. After the short delay to allow for surface sterilization, clamps 70, 71 may be actuated in the direction of arrows (E,F). The spike tube is designed to pierce the membrane tube and continue to enter the membrane tube until actuation is complete.

FIGS. 6A-6D illustrate a device to vial sterile assembly (as opposed to a sterile connection) using a variation of the disclosed method. Such an assembly is described in copending U.S. patent application Ser. No. 09/153,569, the disclosure of which is hereby incorporated by reference. Obviously, with the spike and membrane configuration there is no need to cut-off the ends of these components in the process.

As stated previously, "assembly" of two components differs from "connection" of two components in that a fluid pathway is not immediately established with assembly. Where two drug components are to be combined, it is sometimes the case that the components separately have longer shelf-lives than when combined to form the final product. In such instances, it may be desirable to package the drug component containers as assembled rather than as connected, especially where it is anticipated that the assembled components may be stored for a period of time. A suitable connection (i.e., creation of a fluid pathway) may be readily achieved in the field (e.g., hospitals, clinics, etc.) by trained personnel prior to use.

Figure 7A:
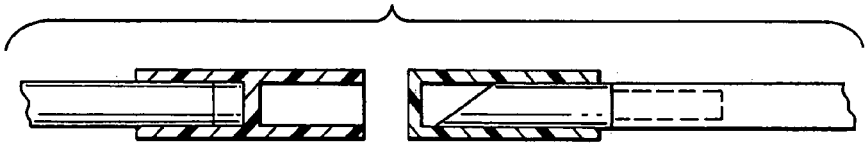
FIGS. 7A through 7E are alternative embodiments and variations on the spike tube and membrane tube configured ends.
Figure 7B:
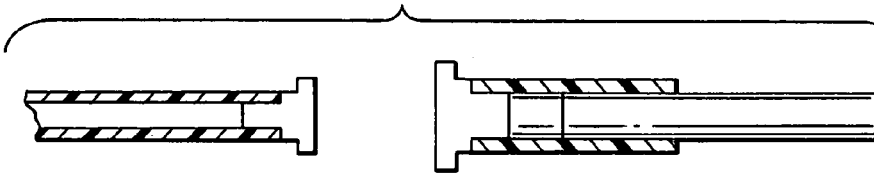
Figure 7C:
Figure 7D:
Figure 7E:
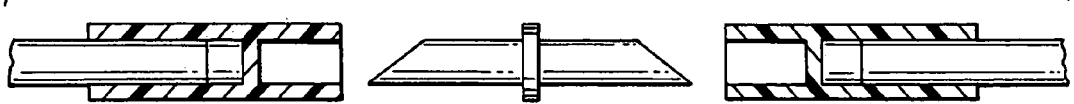

Alternatives to and variations of the spike and membrane tubes, shown in FIG. 5B and used in a preferred embodiment of the present invention, are abundant in the art. Some of these alternatives which do not require end cut-off are illustrated in FIGS. 7A-7E. For example, FIG. 7A shows the spike end having a tip protector. FIG. 7B illustrates removable plugs in each end. These plugs may insert into the inner diameter of the ends, or, as illustrated, over the outer diameter of the ends. FIG. 7C shows seal tabs used as closures on the ends. FIG. 7D illustrates another variation of the spike and membrane configuration. FIG. 7E, also a variation of the spike and membrane configuration, introduces a dual end spike component. Generally, the illustrated configuration may be varied where one component may have a larger inner diameter of the sealed terminal end than the outer diameter of the sealed terminal end of the other component, such that the smaller fits snugly into the larger. Also, the ends 14 may be of an identical diameter, but be brought together to abut each other within a collar (not shown). To the extent that such alternative designs, too numerous to illustrate, allow pre-sterilized ends to be brought together within a sterile field, creating a sterile connection between the ends, such alternatives are considered to fall within the scope of the present invention.

Regardless of the design configuration of terminal ends 14, a permanent seal between the contacting ends will need to be effected. The final permanent connection is preferably made outside the sterile field, but, if necessary, can also be accomplished while the contacting ends are exposed within the e-beam field sphere 60. This connection can be made using a radio frequency sealer (such as a HEMATRON™), a heat sealer, solvent bonding techniques, or the like.

Figure 8A:
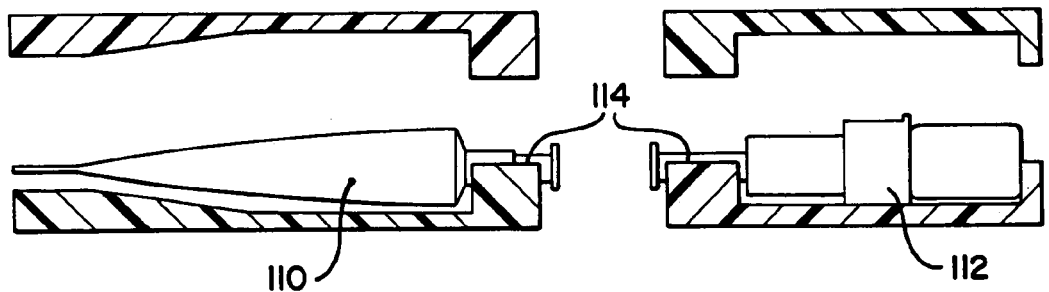
FIGS. 8A through 8D illustrate an alternative connection using a stream of hot air to soften membrane tubes which are then brought together to join as they cool.
Figure 8B:
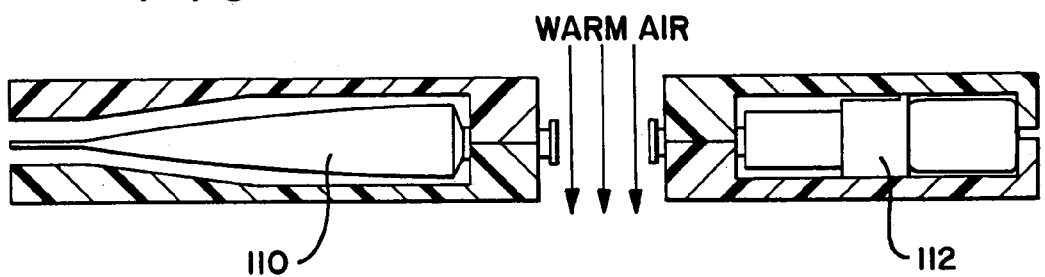
Figure 8C:
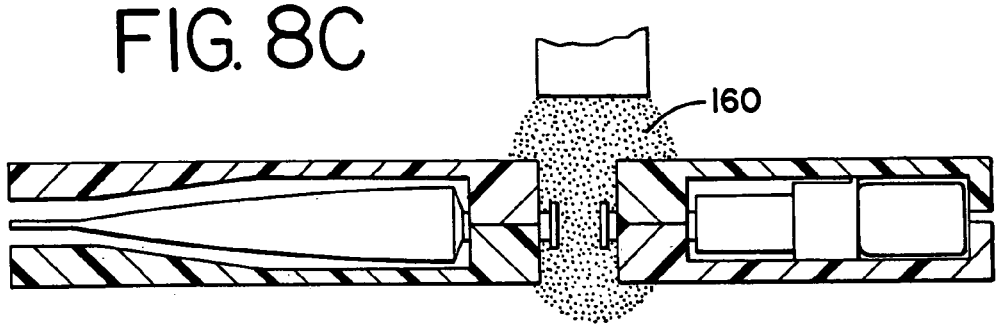
Figure 8D:
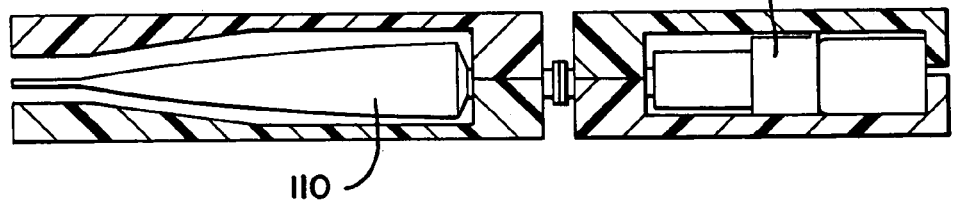

In an alternate method, shown in FIGS. 8A-8D, a device to vial assembly (similar to the assembly shown in FIG. 6D) connection is illustrated with some variation to the methods previously discussed. FIG. 8A shows device 110 and vial assembly 112, both having membrane tubes 114, positioned for sterile connection. The membrane tube 114 of each component is subjected to a hot air stream, as shown in FIG. 8B. The membrane of each tube 114 becomes semi-amorphous, and the tubes 114 are moved toward one another, as shown in FIG. 8C, within e-beam field sphere 160. FIG. 8D shows the final connection, where the membrane tubes have been held together until cool enough to form a proper seal.

Figure 9:
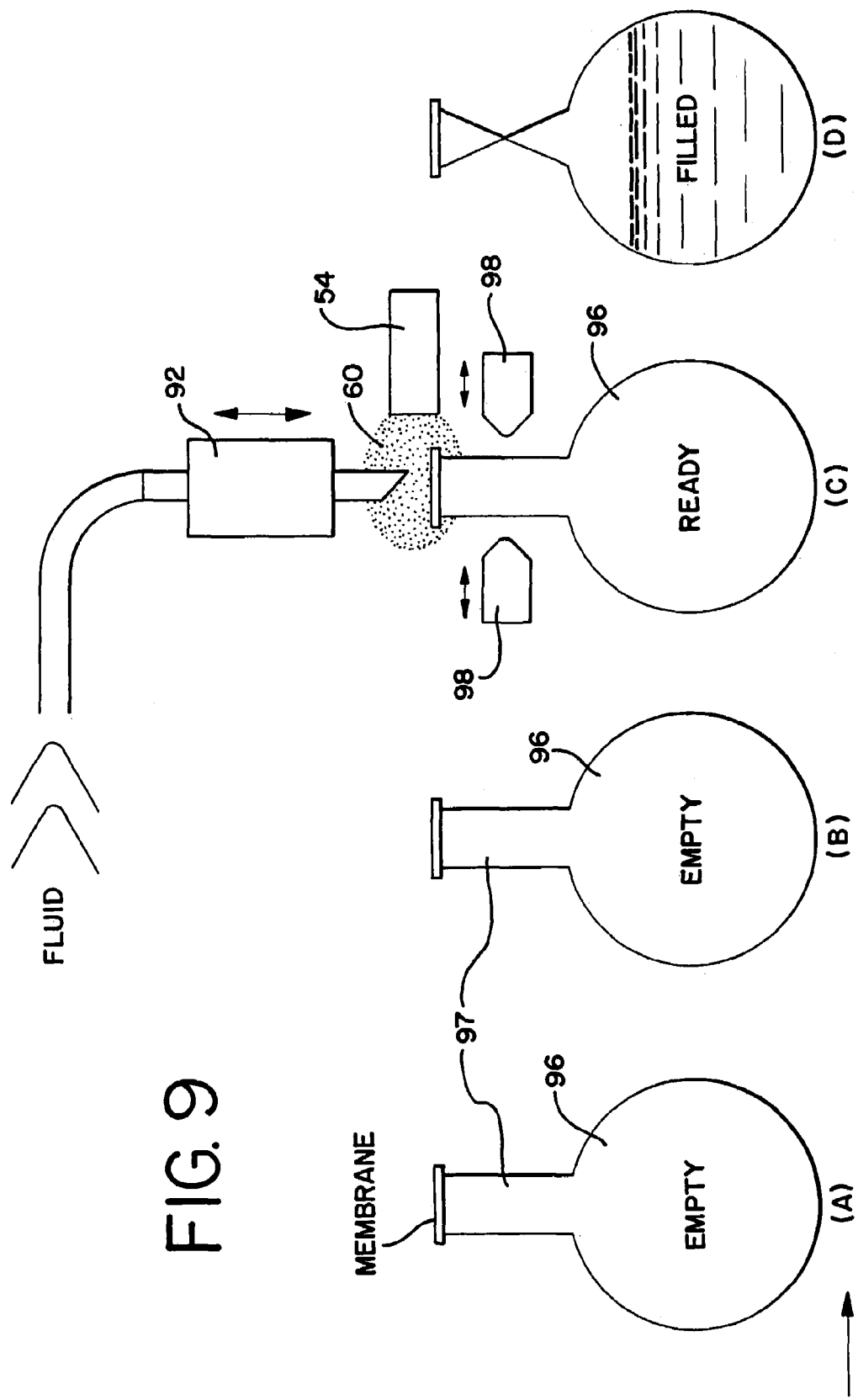
FIG. 9 illustrates the sterile fill process of the present invention.

Another variation is shown in the sequenced illustration of FIG. 9, in which the present invention is used for a sterile fill process. A bulk fluid container (not shown) preferably has a piercing valve of some type, generally illustrated as 92, for dispensing a pre-sterilized liquid within held within the container. While maintaining valve 92 within an active sterile field 60, empty pre-sterilized containers 96 having an inlet port 97 covered preferably by a thin membrane (not shown) may be positioned, as shown at points (A) and (B), to travel toward the dispensing valve 92 of the container to receive an aliquot of sterile liquid. Upon reaching the dispensing valve 92, as shown at point (C), the inlet port 97 and membrane are held within the sterile field 60 aligned with dispensing valve 92 to effect sterilization of the outer surfaces. Then, dispensing valve 92, having a spiked end, moves to pierce or breach the membrane of inlet port 97 within sterile field 60, and filling may begin. Inlet port 97 is maintained within sterile field 60 until the pre-sterilized container 96 is sufficiently filled. Inlet port 97 may then be sealed by sealer 98 and removed from the sterile field 60, as shown at point (D).

Alternatively, however, returning to the drawing of FIG. 2, after components 10, 12 are connected by bringing their respective ends in contact with one another, the components 10, 12 can be moved to sealing station 80. Here the contacting ends may be sealed using available technology to form a weld, as known in the art. For instances, the material of both ends may be melted. Then the ends can be pressed together by actuation of clamps 70, 71, and cooled to form a seal. After sealing, the connected components 10, 12 may be packaged for shipment, storage, immediate use, or any other purpose.

While specific embodiments have been illustrated and described, numerous modifications are possible without departing from the spirit of the invention, and the scope of protection is only limited by the scope of the accompanying claims.

We claim:

1. A method for the sterile joining of two or more pre-sterilized components comprising the steps of:
   a. sterilizing an end of each component to be joined together within an active sterile field;
   b. preparing the end of each component to be joined while exposed to the active sterile field; and
   c. moving the end of at least one of the components while exposed to the active sterile field to thereby join the prepared ends together while exposed to the active sterile field.

2. The method of claim 1, wherein the step of preparing includes the step of opening an end of each component to be joined.

3. The method of claim 1, wherein the step of sterilizing comprises the steps of:
   a. creating an electron beam field to produce an active sterile field; and
   b. positioning the ends within the electron beam field.

4. The method of claim 3, wherein the step of creating an electron beam field comprises the step of establishing the field at a voltage of less than 300 KeV.

5. The method of claim 4, wherein the electron beam field is established within the range of from about 30 to about 300 KeV.

6. The method of claim 4, wherein the electron beam field is established within the range of from about 30 to about 100 KeV.

7. The method of claim 6, wherein the electron beam field is established at about 60 KeV.

8. The method of claim 1, wherein the step of sterilizing comprises the steps of:
   a. creating a chemical vapor atmosphere to produce an active sterile field; and
   b. positioning the ends within the chemical vapor atmosphere.

9. The method of claim 8, wherein the step of creating a chemical vapor atmosphere comprises the step of selecting a suitable chemical compound from the group comprising hydrogen peroxide, peracetic acid, and chlorine dioxide.

10. The method of claim 1, wherein the step of sterilizing comprises the steps of:
    a. pulsing a high-energy light with a large ultraviolet component to produce an active sterile field; and
    b. positioning the ends within the pulsed high-energy light.

11. The method of claim 1, wherein the step of sterilizing comprises the steps of:
    a. creating a plasma atmosphere to produce an active sterile field; and
    b. positioning the terminal sealed ends within the plasma atmosphere.

12. The method of claim 11, wherein the step of creating a plasma atmosphere is achieved using ozone.

13. The method of claim 1, wherein the steps of sterilizing, preparing, and joining are automated.

14. The method of claim 2, wherein the step of moving to thereby join comprises the steps of:
    a. inserting an opened end of one component into the opened end of another component to create overlapping sections; and
    b. bonding the overlapping sections together.

15. The method of claim 2, wherein the step of moving to thereby join comprises the steps of:
    a. abutting the opened end of one component with the opened end of another component; and
    b. welding the abutting ends together.

16. The method of claim 1, wherein the step of preparing includes the step of severing at least one component end.

17. The method of claim 1, wherein the step of preparing includes the step of uncapping at least one component end.

18. A method for the sterile assembly of two or more pre-sterilized components together comprising the steps of:
   a. preparing at least one end of each component for assembly;
   b. sterilizing the prepared ends of each component to be assembled together within an active sterile field;
   c. moving at least one of the prepared ends into contact with the other while in the active sterile field; and
   d. assembling the prepared ends together while in the active sterile field.

19. The method of claim 18, wherein the step of preparing the ends includes the steps of removing a cap from at least one of the ends.

20. The method of claim 18, wherein the step of sterilizing comprises the steps of:
   a. creating an electron beam field to produce an active sterile field; and
   b. positioning the ends within the electron beam field.

21. The method of claim 20, wherein the steps of creating an electron beam field comprises the step of stablishing the field at a voltage of no more than 300 Kev.

22. The method of claim 21, wherein the electron beam field is stablished within the range of from about 30 to about 300 KeV.

23. The method of claim 22, wherein the electron beam field is established within the range of from about 30 to about 300 KeV.

24. The method of claim 23, wherein the electron beam field is established at about 60 KeV.

25. The method of claim 18, wherein the steps of sterilizing comprises the steps of:
   a. creating a chemical vapor atmosphere to produce an active sterile field; and
   b. positioning the ends within the chemical vapor atmosphere.

26. The method of claim 22, wherein the step of creating a chemical vapor atmosphere comprises the step of selecting a suitable chemical compound from the group comprising hydrogen peroxide, peracetic acid, and chlorine dioxide.

27. The method of claim 18, wherein the step of sterilizing comprises the steps of:
   a. pulsing a high-energy light with a large ultraviolet component to produce an active sterile field; and
   b. positioning the ends within the pulsed high-energy light.

28. The method of claim 18, wherein the step of sterilizing comprises the steps of:
   a. creating a plasma atmosphere to produce an active sterile field; and
   b. positioning the ends within the plasma atmosphere.

29. The method of claim 25, wherein the step of creating a plasma atmosphere is achieved using ozone.

30. A system for effecting the sterile joining of at least two pre-sterilized components together comprising
   a. an active sterile field for encompassing at least one end of each component to be joined together;
   b. a surface for supporting ends of the components within the active sterile field;
   c. a mechanism which opens an end of at least one of the components while the end is supported by the surface in the active sterile field;
   d. a mechanism which moves at least one of the component ends into aligned contact with the other while maintaining the at least one open component end in the active sterile field; and
   e. a sealing device for bonding the aligned ends together.

31. The system of claim 30, wherein the mechanism which moves at least one of the component ends into aligned contact comprises at least one mechanical actuator.

32. The system of claim 31, wherein the low voltage electron beam instrument operates within the range of from about 30 KeV to about 300 KeV.

33. The system of claim 31, wherein the low voltage electron beam instrument operates within the range of from about 60 KeV to about 100 KeV.

34. The system of claim 30, wherein the active sterile field is created by a chemical vapor atmosphere.

35. The system of claim 34, wherein the chemical vapor atmosphere is created by a chemical selected from the group of chemicals including hydrogen peroxide, peracetic acid, and chlorine dioxide.

36. The system of claim 30, wherein the active sterile field is created by a pulsed high-energy light source having a large ultraviolet component.

37. The system of claim 30, wherein the active sterile field is created by a plasma atmosphere.

38. The system of claim 30, wherein the mechanism which brings the opened ends into contact is mechanically actuated.

39. The system of claim 38, wherein the mechanical actuation is automated.

40. The system of claim 30, wherein the surface for supporting is automated.

* * * * *